United States Patent [19]

Kifune et al.

[11] Patent Number: 5,290,752

[45] Date of Patent: Mar. 1, 1994

[54] METHOD FOR PREPARATION OF A SHAPED CHITIN BODY CONTAINING A PHYSIOLOGICALLY ACTIVE SUBSTANCE

[75] Inventors: Koji Kifune, Nara; Kenzo Motosugi; Hiroyuki Tanae, both of Kyoto, all of Japan

[73] Assignee: Unitika Ltd., Hyogo, Japan

[21] Appl. No.: 963,256

[22] Filed: Oct. 19, 1992

Related U.S. Application Data

[63] Continuation of Ser. No. 526,942, May 21, 1990, which is a continuation of Ser. No. 712,489, Mar. 18, 1985, abandoned.

[30] Foreign Application Priority Data

Mar. 16, 1984 [JP] Japan ................... 59-51880

[51] Int. Cl.$^5$ .............................................. A01N 25/10
[52] U.S. Cl. ................................. 504/116; 424/408; 424/488; 514/777
[58] Field of Search .............. 71/DIG. 1; 514/55, 777; 424/488, 408; 504/116; A01N 25/10

[56] References Cited

U.S. PATENT DOCUMENTS

| | | | |
|---|---|---|---|
| 3,911,098 | 10/1975 | Capozza | 424/428 |
| 4,007,258 | 2/1977 | Cohen et al. | 424/22 |
| 4,059,457 | 11/1977 | Austin | 106/203 |
| 4,267,280 | 5/1981 | McCormick, II | 525/56 |
| 4,267,281 | 5/1981 | McCormick, III | 525/61 |
| 4,282,209 | 8/1981 | Tocker | 514/477 |
| 4,376,199 | 3/1983 | Koshugi | 536/20 |
| 4,378,017 | 3/1983 | Koshugi et al. | 424/35 |
| 4,389,331 | 6/1983 | Samejima et al. | 424/35 |
| 4,536,207 | 8/1985 | McCandliss et al. | 71/88 |
| 4,704,268 | 11/1987 | Kifune | 424/488 |

FOREIGN PATENT DOCUMENTS

| | | |
|---|---|---|
| 0013181 | 7/1980 | European Pat. Off. ...... C08B 37/08 |
| 0021750 | 7/1981 | European Pat. Off. . |

OTHER PUBLICATIONS

Chemical Abstracts, vol. 101, No. 14, Oct. 1, 1984, p. 66 No. 112325v.
Patent Abstracts of Japan, vol. 3, No. 55 (C-45), May 11, 1979, p. 141 C 45 and JP-A-54 31 458 of Mar. 8, 1979.
McCormick I. CAS 96:81186x, 1980.
McCormick, C. L. IV et al (1984) CA 101:186132b.
McCormick et al V, "Homogenous Solution, etc" *J. Polymer Science* 17 494 (1979).
Unitika, "Chitin dopes." (1984) CA 101:112326w (1984).
Miyazaki et al, "The use of chitin, etc;" (1981) *Chem. Pharm. Bull.*, vol. 29, pp. 3067-3069 (1981).
Teijin, "Solubilizing drugs by size, etc.," (1984) CA 100:126927j (1984).
Chang et al, "Effects of water removal, etc;" (1980) CA 94:152614g (1981).

*Primary Examiner*—Richard L. Raymond
*Assistant Examiner*—S. Mark Clardy
*Attorney, Agent, or Firm*—Sughrue, Mion, Zinn, Macpeak & Seas

[57] ABSTRACT

A shaped chitin body containing a high content of a physiologically active substance, such as a drug to be used for the cure or prevention of disease, is prepared by incorporating said physiologically active substance into a dope comprising (a) a water-insoluble chitin, (b) lithium chloride, and (c) N-methylpyrrolidone and/or dimethylacetamide, with the amount of said physiologically active substance incorporated being 0.5 wt. % or more with respect to the amount of the chitin contained in said dope, and thereafter coagulating the resulting mixture with a coagulant to obtain a shaped body.

The high content of the physiologically active substance thus incorporated in the shaped chitin can be slowly released therefrom over a long period of time. The shaped-chitin of the present invention is characterized by long duration of the physiological activity of the active substance contained therein.

12 Claims, No Drawings

METHOD FOR PREPARATION OF A SHAPED CHITIN BODY CONTAINING A PHYSIOLOGICALLY ACTIVE SUBSTANCE

This is a continuation of application Ser. No. 07/526,942, filed May 21, 1990, which is a continuation application of application Ser. No. 06/712,489, filed Mar. 18, 1985, now abandoned.

FIELD OF THE INVENTION

The present invention relates to a method for preparation of a shaped chitin body containing a high content of a physiologically active substance, which substance can be slowly released therefrom and lasts for a long period of time.

BACKGROUND OF THE INVENTION

Various methods have heretofore been proposed for the purpose of prolonging the effective life of physiologically active substances, where a physiologically active substance is contained in a carrier of a polymeric substance. In particular, a natural polymeric substance such as a cellulose or a starch is proposed as being preferable as a carrier in such case in a form wherein the physiologically active substance-containing carrier is used as found in nature and therefore must be safe. Such natural polymeric substances include a chitin of an amino-polysaccharide. In this connection, U.S. Pat. No. 3,911,098, corresponding to Japanese Patent Application (OPI) No. 123815/75 (The term "OPI" as used herein refers to a "published unexamined Japanese patent application".) discloses a drug-releasing instrument, where a drug is incorporated in a chitin solution and the resulting mixture is shaped to form a shaped body which may slowly release the effective ingredient of the incorporated drug. This prior art technique, however, has some problems, in that the chitin component used therein is a water-soluble chitin derivative, and therefore, when said drug-releasing instrument is used in the presence of water, the carrier itself is dissolved and the effect of the physiologically active substance contained therein does not last for a long period of time.

The present inventors have conducted extensive studies to overcome the above-mentioned problem and to obtain a biolytic drug-releasing body comprising a water-insoluble chitin as a carrier, and as a result, previously proposed a method where a physiologically active substance is incorporated in a swelled body of a water-insoluble chitin, as described in U.S. application Ser. No. 637,191, filed Feb. 8, 1984, now U.S. Pat. No. 4,704,268, corresponding to Japanese Patent Application No. 145428/83). However, this prior art process still involves a problem in that a physiologically active substance can generally not be incorporated in the carrier at a desirably high concentration.

A shaped chitin body containing a physiologically active substance at a high concentration is disclosed in *Chem. Pharm. Bull.*, Vol. 29, pp. 3067–3069 (1981), where a chitin is dissolved in hexafluoro-2-propanol, and a drug is added thereto in an amount of 200 wt. % with respect to the amount of the chitin, and thereafter the solvent is evaporated to obtain drug-containing chitin-tablets. However, the solvent used in this method is extremely specific and expensive, and is highly toxic. In addition, the retention percentage of the physiologically active substance in the formed tablets is 25% or less, and the duration for releasing the active substance is almost within 24 hours.

U.S. Pat. No. 4,059,457 discloses a method for preparing a shaped chitin body, wherein a chitin is dissolved in a lithium chloride-containing dimethylacetamide solution or in a lithium chloride-containing N-methylpyrrolidone solution, and the resulting chitin-dope is coagulated with a coagulant to obtain a shaped chitin body. However, there is no disclosure in U.S. Pat. No. 4,059,457 with respect to a method where a physiologically active substance is incorporated in a chitin-dope.

SUMMARY OF THE INVENTION

The present inventors have conducted further studies in order to be able to increase the concentration of physiologically active substance that can be incorporated in a water-insoluble chitin and to obtain a drug-containing chitin which may slowly release the active ingredient therefrom for a long period of time. As a result, the inventors have found that a shaped chitin body which may contain a large amount of a physiologically active substance can be obtained by incorporating said active substance in a dope obtained by dissolving a water-insoluble chitin in a specific solvent, and thereafter coagulating the resulting mixture with a coagulant, and furthermore that the physiologically active substance contained in the shaped chitin body is not substantially deactivated, and may therefore be slowly released from the shaped chitin body for a long period of time.

The present invention, therefore, provides a method for preparing a shaped chitin body containing a physiologically active substance, comprising incorporating a physiologically active substance in a dope comprising (a) a water-insoluble chitin, (b) lithium chloride, and (c) N-methylpyrrolidone and/or dimethylacetamide, the amount of said physiologically active substance being 0.5 wt. % or more with respect to the amount of the chitin in said dope, and then the resulting mixture is coagulated with a coagulant to form a shaped body.

DETAILED DESCRIPTION OF THE INVENTION

"Water-insoluble chitin" as used in the present invention includes poly(N-acetyl-D-glucosamine) obtained from crustaceans or insects by treating with hydrochloric acid or sodium hydroxide to remove proteins and calcium contents therefrom for purification, and derivatives of said chitin which are insoluble in water. Such derivatives include partly deacetylated chitins (or a part of the acetylamino groups in the chitin are deacetylated), and etherified, esterified, hydroxyethylated, or O-ethylated chitins. Examples of these chitin derivatives include poly[N-acetyl-6-O-(2'-hydroxyethyl)-D-glucosamine], poly N-acetyl-6-O-(ethyl)-D-glucosamine, etc.

In order to obtain a shaped chitin body according to the present invention, a dope is first prepared, comprising (a) said water-insoluble chitin, (b) lithium chloride, and (c) N-methylpyrrolidone or dimethylacetamide or the mixture thereof. The concentration of the lithium chloride is preferably 5 wt. % or more, as this is well soluble in a chitin. Next, a physiologically active substance is incorporated in the thus prepared dope.

"Physiologically active substance" as used in the present invention includes, for example, synthetic and natural drugs to be used for cure and/or prevention of disease; agricultural chemicals such as herbicides, insecticides, plant growth regulators, etc.; perfumes; and enzymes.

Examples of drugs which can be used in the present invention are as follows:

(1) Proteinaceous medicines such as insulin. (2) Agents for combating infections such as antibiotics including pencillins, cephalosporins, polymyxin B, amphotericin B, trichomycin, gramicidin S, colistin, nystatin, kanamycin, chloramphenicol, tetracycline, erythromycin, streptomycin, rifampicin, actinomycin, and chromomycin $A_3$.

(3) Carcinostatic such as carcinophilin, sarkomycin, bleomycin, mytomycine C, nitrogen mustard, nitrogen mustard-N-oxide, cyclophosphamide, merpheran, chlorambucyl, uracil mustard, triethylene melamine, triethylene thiophosphoamide, busulfan, pipobroman, carmustine, dacarbazine, procarbazine, dibromomannitol, dibromodarcitol, azathioprine, 6-mercaptopurin, thioguaninethioisocin, 5-fluorouracil, 5-fluorodeoxyuridine, ftorafur, citracin arabinoside, cyclocytidine, 5-azacytidine, vincristine, vinblastine, podophyllo-folic acid, 4-aminopterin, methotrexate, teropterin, dihydrofolic acid, tetrahydro-folic acid, 6-diazo-5-oxonolylleucin, azaserine, actinomycin C, D, chromomycin $A_3$, daunorubicin, L-asparaginase, adriamycin, and daunomycin.

(4) Ophthalmic curative medicines such as tetracyclin, chlorotetracyclin, bacitracin, neomycin, polymyxin, gramicidine, and oxytetracyclin.

(5) Steroidal contraceptives such as 19-nortestostetone and 17α-hydroxyprogestrone.

Examples of agricultural chemicals are as follows: Pyrethrin, rotenone, nicotine sulfate, benzoepine, EPN (ethyl p-nitrophenyl benzenethiophosphonate), NAC (naphthyl methylcarbamate), MTMC (m-tolyl methylcarbamate), BPMC (butylphenyl methylcarbamate), EPBP (2,4-dichlorophenyl ethyl phenylphosphonothionate), Malathon, MPMC (3,4-xylyl methylcarbamate), Dimethoate, ethylthiomethone, diazinon, DDVP (2,2-dichlorovinyl dimethyl phosphate), DEP (dimethyl 1-hydroxy-2,2,2-trichloroethylphosphonate), Mecarbam, PAP (dimethyl S-[α-(ethoxycarbonyl)benzyl]phosphorothiolothionate), machine oil, PHC (O-isopropoxyphenyl methylcarbamate), MPP (dimethyl 3-methyl-4-methylthiophenyl phosphorothionate), MEP (dimethyl 3-methyl-4-nitrophenyl phosphorothionate), allethrin, MIPC (O-cumenyl methylcarbamate), thiomethane, formothione, DMTP (dimethyl-S-(2-methoxy-5-oxo-1,3,4-thiadiazolin-4-ylmethyl) phosphorothiolothionate), salithion, ESP (dimethyl S-(2-ethylsulfinyl-1-methyethyl)phosphorothiolate), ECP (2,4-dichlorophenyl diethyl phosphorothionate), PMP (dimethyl S-(phthalimidomethyl) phosphorothiolothionate), CYO, CYAP (p-cyanophenyl dimethyl phosphorothionate), CVP (2-chloro-1-(2,4-dichlorophenyl)-vinyl diethyl phosphate) phosalone, BRP (1,2-dibromo-2,2-dichloroethyl dimethyl phosphate), XMC (3,5-xylyl methylcarbamate), cartap, methomyl, ethione, EDB (ethylene dibromide), TCE (tetrachloroethylene), CPCBS (p-chlorophenyl p-chlorobenzene-sulfonate), BCPE (1,1-bis(p-chlorophenyl)ethanol), chlorobenzilate, chloropropylate, kelthane, tetradifone, BPPS (2-(p-tert-butylphenoxy)-cyclohexyl propynyl sulfite), phenisobromolate, D-D (D-D mixture (1,3-dichloropropene, 2-dichloropropane)), EDC (1,2-dichloroethane), DCIP (bis(2-chloro-1-methylethyl)ether), hydrogen cyanide, ammonium phosphate, ethylene oxide, metaldehyde, prochonol, benzomate, CVMP (2-chloro-1-(2,4,5-trichlorophenyl)vinyl dimethyl phosphate), isonaomate, Vamidothion, dialifor, isoxathione, propaphosnotricyclohexyltin hydroxide, pyridaphenthion, acephate, polynactin complex, chloropyriphospmethyl, amitraz, propaphos, dimethylvinphos, pirimicarb, methylisocyanate, pirimiphos-methyl, monocrotophos, resemthrin, oxamyl, copper sulfate, zinc sulfate, copper, organotin compounds, organocopper compounds, captan, organoarsenic compounds, IBP (S-benzyl diisopropyl phosphorothiolate), kasugamycin, copper nonylphenol-sulfonate, EDDP (O-ethyl diphenyl phosphorodithiolate), organonickel compounds, phthalide, sulfur, zineb, maneb, polycarbonate, amobam, propineb, thiuram, ziram, thiadiazone, TPN (tetrachloroisophthalonitrile), difolatan, dichlofluanid, DPC (dinocap), binapacryl, quinomethionate, PCNB (pentachloronitrobenzene), thiophanate, thiophanate-methyl, CNA (2,6-dichloro-4-nitroaniline), triazine, PCB (pentachlorophenol), PCBA (pentachlorobenzyl alcohol), dithianone, hydroxyisoxazole, novobiocin, benzalkonium chloride, polyoxin, blasticidin S, phenazine oxide, DBEDC, benomyl, thiabenzazole, validamycin, procymidone, echlomezole, oxycarboxin, probenazole, isoprothiolan, PCP-copper, dimethirimol, alginic acid, fluoroimide, trifolin, soybean lecithin, formaldehyde, iprodione, methyl bromide, chloropicrin-carbam, mepronil, sodium hypochlorite, anhydrous sodium carbonate, chloroneb, PCP (pentachlorophenol), MCP (2-methyl-4-chlorophenoxyacetic acid), DCMU (3-(3,4-dichlorophenyl)-1,1-dimethylurea), 2-4PA (2,4-dichlorophenoxyacetic acid), CNP (2,4,6-trichlorophenyl 4-nitrophenyl ether), MCPB (4-(4-chloro-2-methylphenoxy)butyric acid), MCPP (2-(4-chloro-2-methylphenoxy)propionic acid), MCC (methyl N-(3,4-dichlorophenyl)carbamate), DCPA (dimethyl 2,3,5,6-tetrachloroterephthalate), NIP (nitrofen), DBN (2,6-dichlorobenzonitrile), DCBN (2,6-dichlorothiobenzamide), ACN (2-amino-3-chloro-1,4-naphthoquinone), TCBA (2,3,6-trichlorobenzoic acid), BPA, CAT (2-chloro-4,6-bis(ethylamino)-S-triazine), prometryn, atrazine, ametryn, simetryne, benthiocarb, linuron, diphenamid, trifluralin, MBPMC (2,6-di-tert-butyl-4-methylphenyl N-methylcarbamate), benfluralin, phenmedipham, vernolate, alachlor, ioxynil, SAP (bensulide), lenacil, PAC (phenacridan chloride), DPA (2-2dichloropropionic acid), IPC (chloropropham), paraquat, diquat, bromacil, MDBA (2,6-di-tert-butyl-4-methylphenyl N-methylcarbamate), ethanolamine, isopropenolamine, DNBPA (2-sec-butyl-4,6-dinitrophenyl acetate), siduron, cyanates, chlorate, TCA (trichloroacetic acid), sulfamates, tetrapion, DSMA, TCTP (dimethyl 2,3,5,6-tetrachloroterephthalate), phenothiol, picloram, terbacil, molinate, asulam, oxadiazone, butachlor, chlomethoxynil, propyzamide, nitralin, bentazon, orthobencarb, dymron, napropamid, dimethametryn, piperophos, thiochloromethyl, aziprophosmethyl, glyphosate, alloxydim, and pyrazolate.

Examples of plant growth regulators are α-naphthalene acetic acid, maleic hydrazide, indole-butyric acid, α-naphthylacetamide, 2,4-PA and N-(dimethylamino)-succinamic acid.

In the present invention, the amount of the physiologically active substance to be incorporated in the dope is 0.5 wt. % or more, preferably 1 wt. % or more, more preferably 3 wt. % or more, most preferably 5 wt. % or more, with respect to the amount of the chitin component in the dope. The amount of said physiologically active substance is preferably larger, as much as possible, but the preferable maximum is 50 wt. % or less in view of the shapability of the doped substance and of the slow releasability of the active substance from the shaped body.

The means for incorporating the physiologically active substance in the dope is not specifically limitative in the present invention, and for example, said active substance in any form of a liquid or a solid may be added to the dope and then blended therewith.

The kind of the physiologically active substance to be added to the dope is not limited to only one kind, but two or more kinds of said substances may be incorporated therein. Thus, plural kinds of physiologically active substances may be incorporated in the dope, in accordance with the intended use of the shaped chitin body.

In the present invention, the dope thus containing the physiologically active substance is then coagulated with a coagulant, to finally form a shaped body. The coagulation means is not specifically limitative, but any conventional means may appropriately be applied thereto. Preferred coagulants include, for example, water, alcohols such as methyl alcohol, ethyl alcohol, propyl alcohol and butyl alcohol, and ketones such as acetone. Such coagulants preferably do not dissolve the above-mentioned physiologically active substances.

The shaped chitin body thus prepared according to the present invention may be dried, if required, or may be used in such state as dipped in the coagulant, in accordance with the intended use of said body.

The term "shaped" body as used in the present invention includes fibrous-, sheet-like, firmy, rod-like, spherical, granular and powdery bodies which can be made by means of a wet shaping process.

The shaped body obtained according to the present invention contains a physiologically active substance in an amount of 0.5 wt. % or more, preferably 1 wt. % or more, more preferably 3 wt. % or more, most preferably 5 wt. % or more, with respect to the amount of the chitin contained in said body, without deactivation of said active substance. The shaped body may slowly release the physiologically active substance when put in a moist environment. When the shaped body is administered to a living body or applied to an ecosystem, the physiologically active substance may be slowly released therefrom together with the decomposition of the chitin by an enzyme existing in said living body or in said ecosystem, which is one characteristic of the present shaped body.

For example, the shaped body of the present invention containing a carcinostatic active ingredient as mentioned above is applied to a carcinoma patient by embedding said body in the nearest position from where a carcinomatous tissue was excised, whereby metastasis of carcinoma may be prevented. Thus, the present shaped body is used for treatment including prevention of metastatic carcinoma. The shaped body of the present invention containing a herbicide as mentioned above may be applied to a soil, whereby the herbicidal activity may effectively be maintained for a long period of time.

The shaped chitin body embedded in a living body is, while releasing the physiologically active ingredient thereinto, gradually decomposed due to lysozyme existing in the living body, and therefore, it is unnecessary to remove the used chitin-body therefrom. The shaped chitin body applied in the ecosystem, such as to soil, is gradually decomposed by soil bacteria, and is free from any problem due to remaining in the soil.

The present invention will now be explained in more detail in the following examples.

EXAMPLE 1

Chitin powder (by Kyowa Yushi KK) was milled to a 100-mesh powder, and the resulting fine powder was treated with 1N-HCl for one hour at 4° C. and then heated at 90°-100° C. for three hours in 3% NaOH solution, thereby to remove calcium components and proteins from the chitin powder, and thereafter the thus purified chitin powder was repeatedly rinsed with water and then dried.

The thus-obtained pure chitin was dissolved in an N-methyl-pyrrolidone solution containing 7 wt. % of lithium chloride, at room temperature, the content of said chitin being 8 wt. %, to obtain a highly viscous and transparent dope. To this dope was added trypsin, in an amount of 9 wt. % with respect to the chitin, and the trypsin was uniformly dispersed therein. The thus obtained dope was put in a tank and conveyed by means of a gear pump under pressure and extruded out into methanol as a coagulant through a nozzle of 50 holes (diameter: 0.07 mm$\phi$), at last to obtain multi-fibers, each having a diameter of 25 $\mu$m. These were washed well with methanol, cut into pieces of 10 mm long, and dispersed in water, to form a bonded fabric. The trypsin activity contained in the bonded fabric was determined using milk casein as a substrate, and an increment of TCA (trichloro-acetic acid)-soluble protein was measured by the Folin-reagent described *J. Biol. Chem.*, vol. 193, pp. 265-275 (1951). As a result, the content of trypsin in the bonded fabric was 8.4 wt. %. Thus, a bonded fabric containing a large amount of trypsin was obtained, and this fabric may be used as protection for an acutely inflamed part, as slowly releasing the trypsin ingredient.

EXAMPLE 2

Chitin powder (by Kyowa Yushi KK) was decomposed with 0.1N-HCl to obtain a chitin having a lower molecular weight. This chitin was added to a dimethylacetamide solution containing 8 wt. % of lithium chloride, in an amount of 10 wt. % to said solution, to obtain a transparent solution. To this solution was added benthiocarb, which is a herbicide for use in a paddy field, in an amount of about 25 wt. % with respect to the amount of the chitin, and blended and and uniformly dispersed. The resulting dispersion was poured into water little by little and coagulated, and the coagulated solid was then repeatedly rinsed with water and thereafter the solvent was removed. The thus-obtained solid was dried and then pulverized to a 30-mesh fine powder. A predetermined amount of the powder was put in water, and the releasing speed of the benthiocarb active active ingredient in water was calculated by measuring the absorbance of 215 nm in the powder-containing solution. As a result, it was noticed that the benthiocarb agent was continuously released into water through about 5 days, and it is concluded that the powder may be used as a herbicidal substance which may slowly release the herbicidal active ingredient therefrom for a long period of time, and thus the herbicidal activity may last for a long time. In particular, the described powder is useful as a herbicide in a paddy field.

EXAMPLE 3

10 g of the same chitin of lower molecular weight as used in the previous Example 2 was dissolved in 990 g of dimethylacetamide solution containing 8 wt. % of lithium chloride, to obtain a chitin dope. To this dope was added 5 g of a crystalline pentachlorophenol (PCP), followed by blending and then dropping into water through a nozzle having a diameter of 3 mm and coagulating in the water to form granules. After vacuum drying, spherical granules having a diameter of about 1 mm were obtained. The chitin-containing granules thus obtained were dipped in methanol and stirred for 3 days, and thus, the amount of PCP released and dissolved into methanol was determined by colorimetric determination with 4-aminoantipyrine. As a result, it was found that the content of PCP in the chitin-granules was 32 wt. %. The thus-obtained granules were applied to a soil, and the herbicidal PCP component was continuously and slowly released therefrom into the soil through two months, and the herbicidal activity lasted through the same period.

EXAMPLE 4

0.1 g of the same chitin of lower molecular weight as used in the Example 2 was dissolved in 9.9 g of N-methylpyrrolidone containing 8 wt. % of lithium chloride to obtain a chitin-dope. To this dope was added 10 mg of a crystalline penicillin (potassium salt) and blended, and then dropped into acetone through a nozzle having a diameter of 3 mm and coagulated therein to form granules. These were washed well with acetone and dried in vacuum, to obtain spherical granules having a diameter of about 1 mm. 20 mg of these granules were put in Erlenmeyer flask having a capacity of 100 ml, and 10 ml of an isotonic sodium chloride solution (a physiologic saline) was added thereto and gently shaken at 37° C., and the isotonic sodium chloride solution was exchanged for a new solution every 6 hours. The penicillin activity in the isotonic sodium chloride solution was determined by means of a paper-disk method using *Staphylococcus aureus* as an indicator strain, and as a result, the penicillin was conformed to be slowly released from the granules into the salt solution through 72+hours.

EXAMPLE 5 AND COMPARATIVE EXAMPLES 1 AND 2

Three test tubes were arranged, each containing 0.1 g of the same chitin of lower molecular weight as used in the Example 2. Each of them was dissolved in (i) 4.9 g of N-methyl-pyrrolidone containing 8 wt. % of lithium chloride (Example 5), (ii) hexafluoro-2-propanol (Comparative Example 1), or (iii) an equi-weight mixture (1/1, by weight) of trichloro-acetic acid and 1,2-dichloroethane (Comparative Example 2), to obtain three kinds of chitin-dopes.

To each dope was added 10 mg of trypsin, followed by blending and then coagulation with isobutanol. After washed, the coagulated solids were dried in vacuum, to obtain three kinds of generally spherical granules. Each kind of granules was dropped in 20 ml of 1 mM-HCl, individually, and stirred for three days in a refrigerator, whereby the trypsin contained in the granules was dissolved out into the HCl solution. The trypsin activity was determined in the every solution, analogously to the above mentioned Example 1, and the results were as follows: (i) In the Example 5 where lithium chloride and N-methylpyrrolidone were used as solvents in the preparation of the chitin-dope, the solution had a high trypsin activity corresponding to 5.1 mg of trypsin. (ii) In the Comparative Example 1, where hexafluoro-2-propanol was used, the solution had only a low trypsin activity corresponding to 0.3 mg of trypsin. (iii) In the comparative Example 2, where a mixture of trichloroacetic acid and 1,2-dichloroethane was used, the solution had no trypsin activity. In view of these experimental data, it is concluded that the use of lithium chloride and N-methylpyrrolidone are preferable in that they do not deactivate trypsin.

EXAMPLE 6 AND COMPARATIVE EXAMPLE 3

1 g of the same chitin of lower molecular weight as used in the Example 2 was dissolved in 49 g of dimethylacetamide containing 8 wt. % of lithium chloride, and then 100 mg of bleomycin was added thereto and blended. About 5 ml of the thus-obtained chitin-dope was put in a disposable 10 ml-syringe (made by TERUMO Co.,) whose top end was cut off, and was extruded out into acetone and coagulated therein. After gently stirring in acetone for about 24 hours and washing, the formed solid was subjected to spontaneous drying, as being left at room temperature for one day, and then dried in vacuum at 30° C. for 18 hours, to finally obtain a bleomycin-containing, shaped chitin body of a football-like form having a short diameter of about 6 mm and a long diameter of about 12 mm (Example 6). On the other hand, about 5 ml of the same chitin-dope was put into a glass bottle having a diameter of 2 cm, and dried in vacuum at 80°-110° C. for 15 hours, to obtain a bleomycin-containing, chitin-shaped body of a disk-like form having a diameter of 2 cm and a thickness of about 0.5 cm (Comparative Example 3).

With respect to each of these shaped bodies, the slow releasability of bleomycin from said body was tested, as follows: 100 ml of a deionized water was put in an Erlenmeyer flask having a capacity of 300 ml, and each chitin-shaped body was added thereto and shaken by reciprocating motion at about 30° C., whereby the bleomycin was released from the body and dissolved out into water. The absorbance of 246 nm of the resulting solution, after shaken, was measured, and the existence of the released bleomycin in the solution was thereby confirmed. In the result, the release of bleomycin from the disk-like shaped body (Comparative Example 3) almost ceased after 4 hours; whereas, the release of bleomycin from the football-like shaped body (Example 6) was found to have continued for 70+ hours.

From these results, it is concluded that the wet shaping process of the present invention to use acetone as a coagulant (Example 6) is superior to the dry shaping process to evaporate the used solvent (Comparative Example 3), as the former gives a shaped body which slowly releases the active ingredient contained therein, and the physiological activity of the shaped body lasts for a long period of time.

While the invention has been described in detail and with reference to specific embodiments thereof, it will be apparent to one skilled in the art that various changes and modifications can be made therein without departing from the spirit and scope thereof.

What is claimed is:

1. A method for preparation of a shaped chitin body containing a physiologically active substance, comprising incorporating a physiologically active substance without deactivation of said active substance and without the occurrence of chemical reaction in a dope comprising the following components (a) to (c): (a) a water-insoluble chitin, (b) lithium chloride and (c) N-methylpyrrolidone or dimethylacetamide or a mixture thereof, with the amount of lithium chloride being 7 to 8 wt. % based on the total weight of components (b) and (c), and the amount of said physiologically active substance incorporated being 0.5 wt. % or more with respect to the amount of the chitin contained in said dope, and thereafter coagulating the resulting mixture with a coagulant without deactivation of said active substance and without the occurrence of chemical reaction to obtain a shaped body.

2. A method for preparation of a shaped chitin body as in claim 1, where said physiologically active substance is selected from drugs to be used for the cure or prevention of disease.

3. A method for preparation of a shaped chitin body as in claim 1, where said physiologically active substance is an agricultural chemical selected from a herbicide, an insecticide, and a plant growth regulator.

4. A method for preparation of a shaped chitin body as in claim 1, wherein the physiologically active substance is incorporated in an amount of 1 wt. % or more with respect to the amount of the chitin contained in said dope.

5. A method for preparation of a shaped chitin body as in claim 2, wherein the physiologically active substance is incorporated in an amount of 1 wt. % or more with respect to the amount of the chitin contained in said dope.

6. A method for preparation of a shaped chitin body as in claim 3, wherein the physiologically active substance is incorporated in an amount of 1 wt. % or more with respect to the amount of the chitin contained in said dope.

7. A method for preparation of a shaped chitin body as in claim 1, wherein the physiologically active substance is incorporated in an amount of 3 wt. % or more with respect to the amount of the chitin contained in said dope.

8. A method for preparation of a shaped chitin body as in claim 2, wherein the physiologically active substance is incorporated in an amount of 3 wt. % or more with respect to the amount of the chitin contained in said dope.

9. A method for preparation of a shaped chitin body as in claim 3, wherein the physiologically active substance is incorporated in an amount of 3 wt. % or more with respect to the amount of the chitin contained in said dope.

10. A method for preparation of a shaped chitin body as in claim 1, wherein the physiologically active substance is incorporated in an amount of 5 wt. % or more with respect to the amount of the chitin contained in said dope.

11. A method for preparation of a shaped chitin body as in claim 2, wherein the physiologically active substance is incorporated in an amount of 5 wt. % or more with respect to the amount of the chitin contained in said dope.

12. A method for preparation of a shaped chitin body as in claim 3, wherein the physiologically active substance is incorporated in an amount of 5 wt. % or more with respect to the amount of the chitin contained in said dope.

* * * * *